US00PP11198P

United States Patent [19]

Zary

[11] Patent Number: Plant 11,198

[45] Date of Patent: Feb. 1, 2000

[54] HYBRID TEA ROSE PLANT NAMED 'JACFETEX'

[75] Inventor: Keith W. Zary, Thousand Oaks, Calif.

[73] Assignee: Bear Creek Gardens, Inc., Medford, Oreg.

[21] Appl. No.: 09/000,726

[22] Filed: Dec. 30, 1997

[51] Int. Cl.[7] ..... A01H 5/00

[52] U.S. Cl. ..... Plt./130

[58] Field of Search ..... Plt./130, 132, 134, Plt./138

[56] References Cited

PUBLICATIONS

UPOV–ROM, 1998/01, Plant Variety Database, GTI Jouve Retrieval Software, Citation for 'JACfetex'.

*Primary Examiner*—Howard J. Locker

*Attorney, Agent, or Firm*—Klarquist Sparkman Campbell Leigh & Whinston, LLP

[57] ABSTRACT

Hybrid tea rose having yellow, edged in orange-pink flowers; attractive, long well shaped bud; long open flowers on long stems; good cut flower production; and glossy, dark green foliage.

1 Drawing Sheet

The present invention relates to a new and distinct variety of rose plant of the hybrid tea class which was originated by me by crossing the variety 'JACyem,' U.S. Plant Pat. No. 9,329, with the variety KORbacol, U.S. Plant Pat. No. 8,617.

The primary objective of this breeding was to produce a new rose variety having the long stems, long bud and large open flower of the female parent combined with the bright yellow flower, good cut rose production and glossy foliage of the male parent. The objective was substantially achieved, along with other desirable improvements, as evidenced by the following unique combination of characteristics that are outstanding in the new variety and that distinguish it from its parents, as well as from all other varieties of which I am aware:

1. Novel, yellow, edged in orange-pink, flowers;
2. Long, well-shaped bud;
3. Large, open flower;
4. Long stems;
5. Good cut flower production;
6. Dark green, glossy foliage.

'JACfetex' is a novel colored greenhouse grown cut rose. Flowers produce this novel color under high summer light intensity and low winter light intensity, where other conditions such as temperature and humidity remain substantially constant. This feature is important to cut rose production and is uncommon among todays commercial cut rose varieties that have a mix of yellow and red or pink on petal edges. 'JACfetex' plants grown in a greenhouse in California produce 160–180 stems per meter, the stems averaging 22–26 inches in length.

Asexual reproduction of this new variety by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent*.—JACyem (U.S. Plant Pat. No. 9,329).

*Pollen Parent*.—KORbacol (U.S. Plant Pat. No. 8,617).

Classification:

*Botanical*.—*Rosa hybrida*.

*Commercial*.—*Hybrid Tea*.

FLOWER

Observations made from specimens grown in a greenhouse environment at Somis, Calif. from January, 1996–August 1997.

Blooming habit: Continuous.

Bud:

*Size*.—One and three-quarter inches long when the petals start to unfurl.

*Form*.—The bud form is long, pointed ovoid.

*Color*.—When sepals first divide, bud color is Yellow Group 13B edged in Red Group 45C. When half blown, the upper sides of the petals are Yellow Group 13C edged in Red Group 45D; and the lower sides of the petals are Yellow Group 13C with a faint edge of Red Group 45D.

*Sepals*.—Color: Green Group 138B. Surface texture: Covered in fine hairs. There are three normally to heavily appendaged sepals. There are two unappendaged sepals with hairy edges.

*Receptacle*.—Color: Green Group 146C. Shape: Funnel. Size: Medium (⅜" long×5/16" wide). Surface: Smooth.

*Peduncle*.—Length: Short (2" to 2½"). Surface: Smooth. Color: Green Group 137A. Strength: Stiff, erect.

Bloom:

*Size*.—Large. Average open size is 4½" to 5".

*Borne*.—Singly.

*Stems*.—Long (22–26"), strong.

*Form*.—When first open: High centered. Permanence: Retains its form to the end; outer petal edges curl back.

*Petalage*.—Number of petals under normal conditions: 25–30.

*Color*.—The upper sides of the petals are Yellow Group 13C with each petal edged in Red Group 45D. The reverse sides of the petals are Yellow Group 13C with a faint edge of Red Group 45D. The base of the petals is small (⅛"×⅛"), intense Yellow Group 13A half moon at the point of attachment. The major color on the upper side is Yellow Group 13C.

*Variegations*.—None.

*Discoloration*.—At the end of the first day: No change. At the end of the third day: Little change. On the plant, during day four and day five, as the flower opens, the Red Group 45D color expands on the upper petal surface. By day seven, the yellow color fades to Yellow Group 13D.

*Fragrance*.—Moderate.

Petals:

*Texture*.—Thick, leathery.

*Shape*.—Round to slightly deltoid.

*Form*.—Tips slightly recurved, edges slightly quilled.

*Arrangement*.—Imbricated. Petaloids in the center are few.

*Persistence*.—Drop off cleanly.

*Lastingness*.—On the plant: Long (7–8 days). As a cut flower: Long (11–12 days).

Reproductive parts:

*Anthers*.—Size: Large. Quantity: Many. Color: Yellow. Arrangement: Regular around styles.

*Filaments*.—Color: Yellow.

*Pollen*.—Color: Gold yellow.

*Styles*.—Color: Reddish.

*Stigmas*.—Color: Greenish-white.

Plant:

*Form*.—Bush.

*Growth*.—Very vigorous; upright; branching; Height at six months in the greenhouse in Somis, Calif. is over six feet. By regular cutting of cut flower stems it has been kept at this height.

*Foliage*.—Number of leaflets on normal mid-stem leaves: Five or seven.

*Size*.—Large. (7"×5½").

*Quantity*.—Abundant.

*Color*.—New foliage: Upper and lower surface: Greyed-Red Group 178A. Old foliage: Upper surface: Green Group 139A. Lower surface: Green Group 139C.

*Shape*.—Pointed oval.

*Texture*.—Upper side: Leathery, glossy.

*Edge*.—Serrated.

*Serration*.—Single, small.

*Petiole rachis*.—Color: Greyed Purple 183A on upper surface, Yellow Green 148B below.

*Petiole underside*.—Smooth with occasional prickles.

*Stipules*.—Long (¾"); serrated, bearded.

*Disease resistance*.—Resistant to mildew and rust under normal growing conditions at Somis, Calif.

Wood:

*New wood*.—Color: Green Group 138B. Bark: Smooth.

*Old wood*.—Color: Green Group 137A. Bark: Smooth.

Prickles:

*Quantity*.—On main canes from base: Ordinary to few. On laterals from main canes: Ordinary to few.

*Form*.—Medium (⅜"); hooked downward.

*Color when young*.—Greyed Red 178A. When old, Greyed Orange 176B.

Small prickles:

*Quantity*.—On main stalks: Many. On laterals: Few.

*Color*.—New, Greyed Red 178A. Old, Greyed Orange 176B.

I claim:

1. A new and distinct variety of rose plant of the hybrid tea class, substantially as herein shown and described, characterized particularly as to novelty by novel yellow, edged in orange-pink flowers; attractive long, well-shaped bud, large open flowers; long stems; good cut flower production; and glossy, dark green foliage.

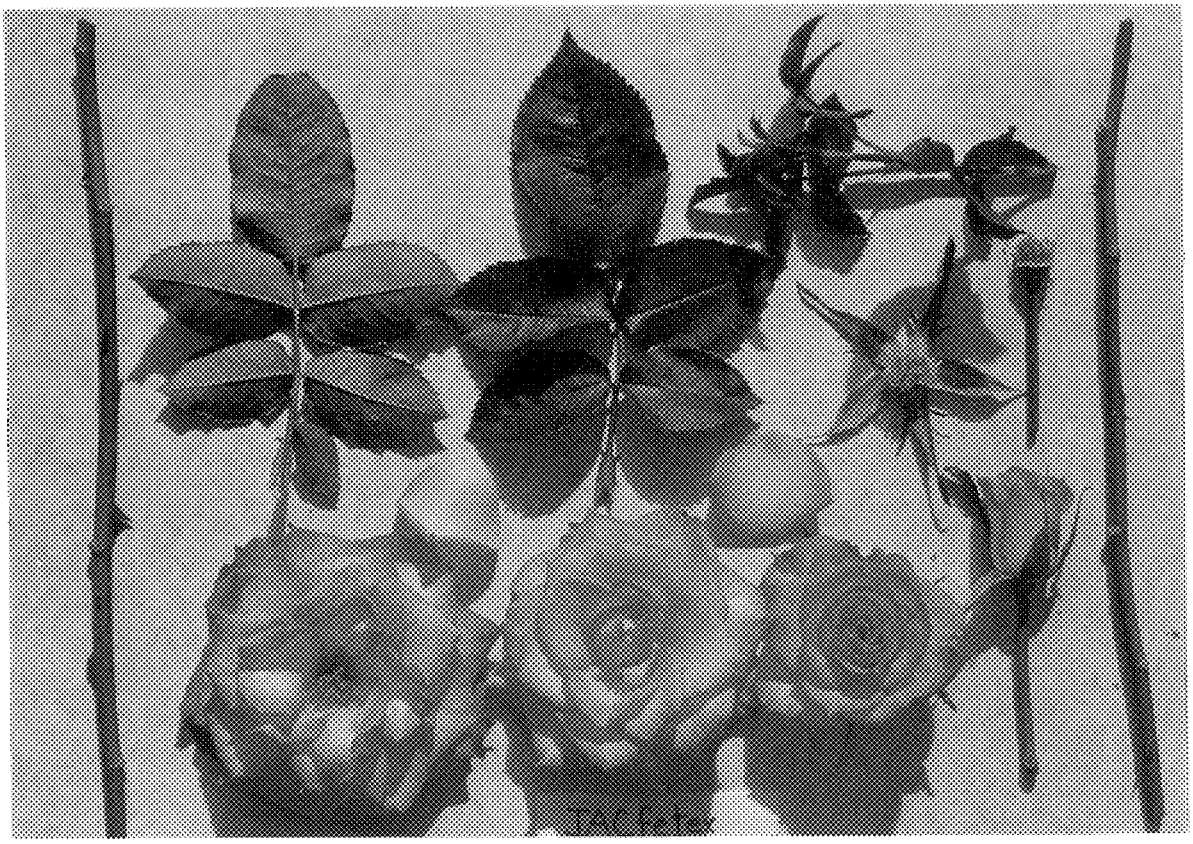

* * * * *